United States Patent [19]

Venkatesan

[11] Patent Number: 5,358,947
[45] Date of Patent: Oct. 25, 1994

[54] ANGIOTENSIN II RECEPTOR BLOCKING 2,3-SUBSTITUTED PYRAZOLO[1,5-A]-1,3,5-TRIAZIN-4(3H)-ONES

[75] Inventor: Aranapakam M. Venkatesan, Elmhurst, N.Y.

[73] Assignee: American Cyanamid Company, Wayne, N.J.

[21] Appl. No.: 120,888

[22] Filed: Sep. 13, 1993

[51] Int. Cl.$^5$ .................. C07D 403/10; A61K 31/53
[52] U.S. Cl. ........................ 514/246; 544/220
[58] Field of Search ................ 544/220; 514/246

[56] References Cited

U.S. PATENT DOCUMENTS

| | | | |
|---|---|---|---|
| 5,162,340 | 11/1992 | Chakravartz | 514/309 |
| 5,202,320 | 4/1993 | Tidwell et al. | 514/218 |
| 5,217,973 | 6/1993 | Bru-Magniez | 514/258 |
| 5,223,501 | 6/1993 | Chakravartz | 514/288 |
| 5,231,094 | 7/1993 | Bau-Magniez | 514/233.2 |
| 5,260,285 | 11/1993 | Allen | 514/81 |

OTHER PUBLICATIONS

Kim, Chemical Abstracts, vol. 106, entry 102327m (1987).

*Primary Examiner*—John M. Ford
*Attorney, Agent, or Firm*—Thomas S. Szatkowski

[57] ABSTRACT

The invention provides novel 2,3-substituted pyrazolo[1,5-a]-1,3,5-triazin-4(3H)-ones having the formula:

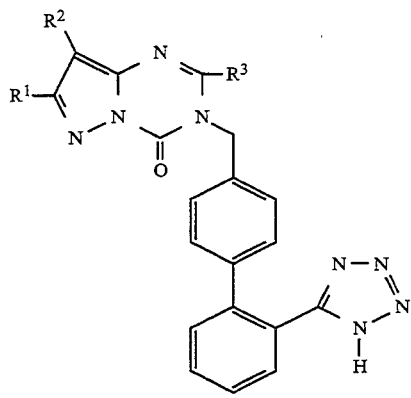

wherein R$^1$, R$^2$ and R$^3$ are described in the specification which have activity as angiotensin II (AII) antagonists.

20 Claims, No Drawings

ANGIOTENSIN II RECEPTOR BLOCKING 2,3-SUBSTITUTED PYRAZOLO[1,5-A]-1,3,5-TRIAZIN-4(3H)-ONES

BACKGROUND OF THE INVENTION

1. Field of the Invention

This invention relates to 2-(lower alkyl)-3-(substituted)-pyrazolo[1,5-a]-1,3,5-triazin-4(3H)-ones which have demonstrated activity as angiotensin II (AII) antagonists and are therefore useful in alleviating angiotensin induced hypertension and for treating congestive heart failure.

SUMMARY OF THE INVENTION

According to the present invention there are provided novel 2,3-substituted-pyrazolo[1,5-a]-1,3,5-triazin-4(3H)-ones of Formula I which have angiotensin II antagonizing properties and are useful as antihypertensives:

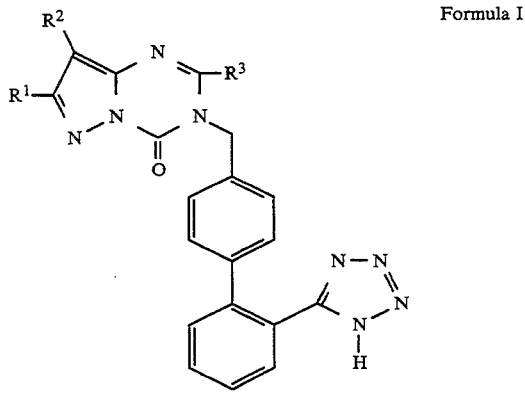

Formula I wherein:

$R^1$ is selected from H, lower alkyl of 1 to 4 carbon atoms, phenyl, substituted phenyl, (substitution selected from mono-lower alkyl of 1 to 3 carbon atoms, trifluoromethyl, nitro, O-alkyl of 1 to 3 carbon atoms, F, Cl, and Br), pyridinyl, thienyl, furanyl, Br and Cl;

$R^2$ is selected from H, lower alkyl of 1 to 4 carbon atoms, phenyl, substituted phenyl, (substitution selected from mono-lower alkyl of 1 to 3 carbon atoms, trifluoromethyl, nitro, O-alkyl of 1 to 3 carbon atoms, F, Cl and Br), pyridinyl, thienyl, furanyl, Br and Cl;

$R^3$ is lower alkyl of 3 to 5 carbon atoms; or the pharmaceutically acceptable salts thereof.

The present invention also provides novel intermediate compounds, methods for making the novel 2,3-substituted-pyrazolo[1,5-a]-1,3,5-triazin-4(3H)-one angiotensin II antagonizing compounds, methods of using the novel 2,3-substituted-pyrazolo[1,5-a]-1,3,5-triazin-4(3H)-one angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

SCHEME I

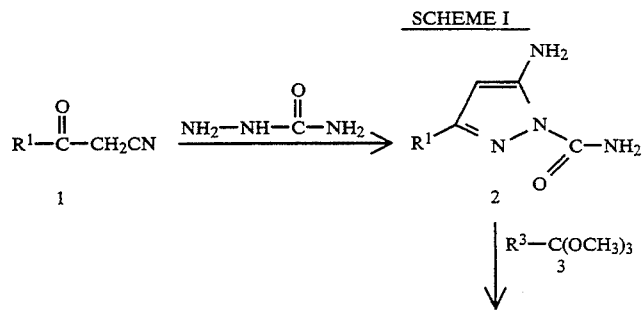

SCHEME I
-continued

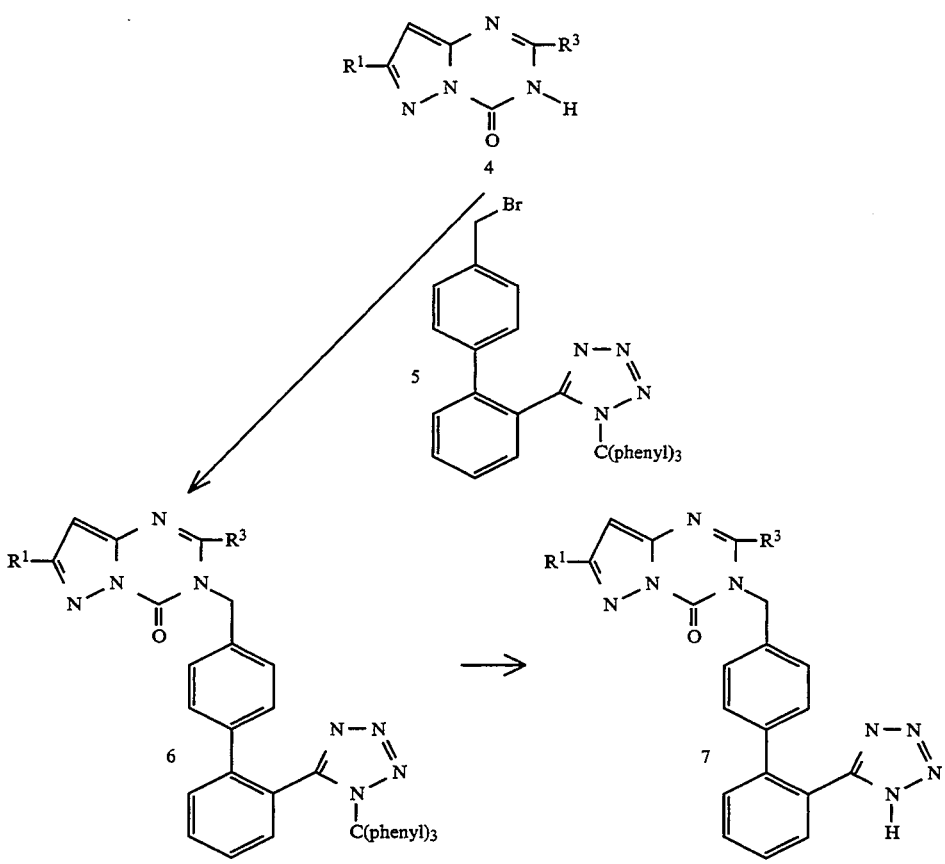

Referring to Scheme I, the substituted acetonitrile 1, where $R^1$ is hereinbefore defined is reacted with semicarbazide hydrochloride in the presence of sodium methoxide in ethyl alcohol followed by reflux to give the 5-amino-3-(substituted)-1H-pyrazole-1-carboxamide 2. 5-Amino-3-(substituted)-1H-pyrazole-1-carboxamide 2 is heated at reflux with trimethylortho ester 3 where $R^3$ is hereinbefore defined to give the 2-substituted-7-substituted-pyrazolo[1,5-a]-1,3,5-triazin-4(1H)-one 4, where $R^1$ and $R^3$ are hereinbefore defined. Biphenyl 5 is coupled to 4 by dissolving in acetone or other suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium diisopropylamide (LDA) or lithium hexamethyldisilazide for 8–24 hours, at 20°–60° C. The obtained alkylated pyrazolo[1,5-a]-1,3,5-triazin-4(3H)-one 6 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(3H)-one 6 with a catalytic amount of hydrochloric acid or other suitable acid such as sulfuric, trifluoroacetic or hydrogen chloride for 2–24 hours gives 7. Additionally, heating 6 in tetrahydrofuran-methanol removes the trityl protecting group and affords 7.

As outlined in Scheme II, 2-substituted-7-substituted-pyrazolo[1,5-a]-1,3,5-triazin-4(1H)-one 4, is brominated in chloroform acetic acid with bromine to give 8. Biphenyl 5 is coupled to 8 by dissolving in acetone or other suitable solvent such as N,N-dimethylformamide, N,N-dimethylacetamide, N-methylpyrrolidinone, methanol, ethanol, t-butanol, tetrhydrofuran, dioxane, or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium diisopropylamide (LDA) or lithium hexamethyldisilazide for 8–24 hours, at 20°–60° C. The obtained alkylated pyrazolo[1,5-a]-1,3,5-triazin-4(3H)-one 9 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(3H)-one 9 with a catalytic amount of hydrochloric acid or other suitable acid such as sulfuric, trifluoroacetic or hydrogen chloride for 2–24 hours to give 10. Additionally, heating 9 in tetrahydrofuran-methanol removes the trityl protecting group and affords 10.

SCHEME II

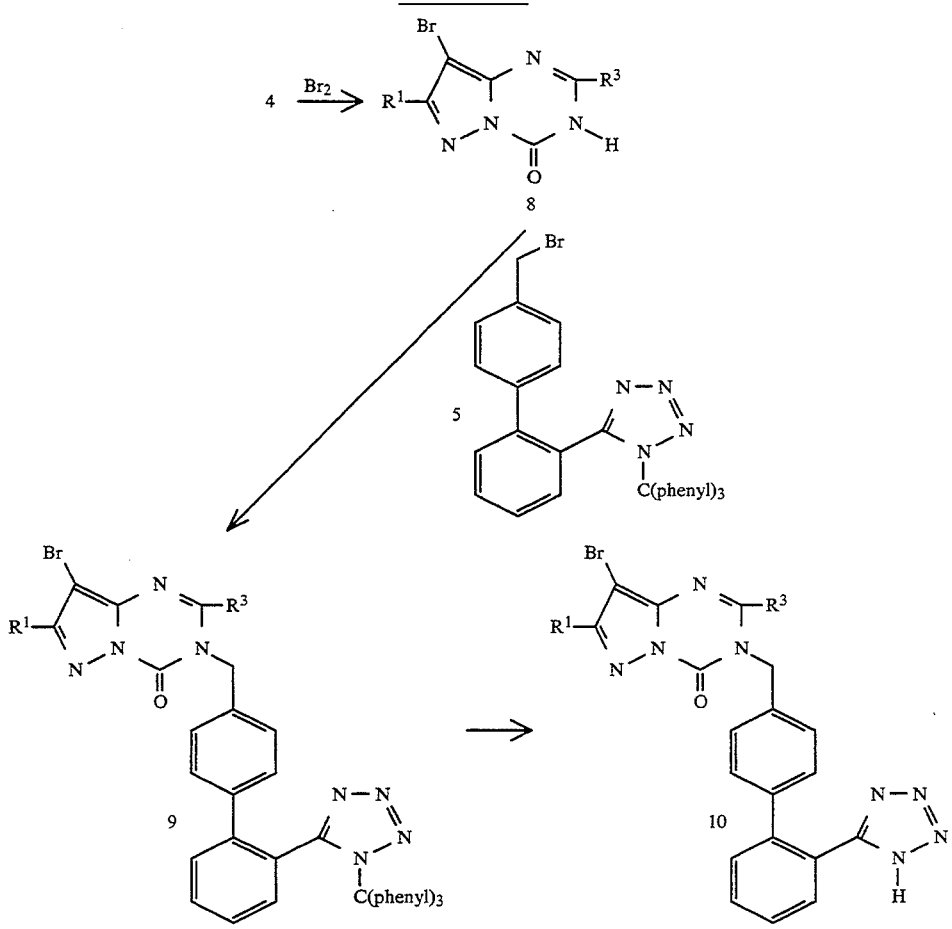

As shown in Scheme III, semicarbazide hydrochloride is reacted with N,N-diethylacrylonitrile in ethyl alcohol at reflux for 6 hours to give 2-(2-cyanoethenyl)-hydrazinecarboxamide 11. Heating 11 in ethyl alcohol in the presence of triethylamine over 4 hours gives 5-amino-1H-pyrazole-1-carboxamide 12. Reaction of 12 with orthoester 3 at 100° to 130° C. gives the 2-substituted-pyrazolo[1,5-a]-1,3,5-triazin-4(1H)-one 13. Biphenyl 5 is coupled to 13 by dissolving in acetone or other suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) of lithium diisopropylamide (LDA) or lithium hexamethyldisilazide for 8-24 hours, at 20°-60° C. The obtained alkylated pyrazolo[1,5-a]-1,3,5-triazin-4(1H)-one 14 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(1H)-one 14 with a catalytic amount of hydrochloric acid or other suitable acid such as sulfuric, trifluoroacetic or hydrogen chloride for 2-24 hours to give 15. Additionally, heating 14 in tetrahydrofuran-methanol removes the trityl protecting group and affords 15.

SCHEME III

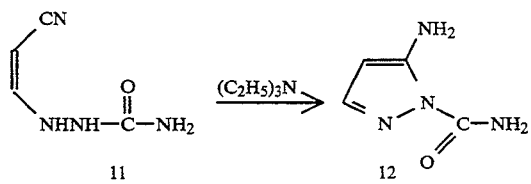

SCHEME III -continued

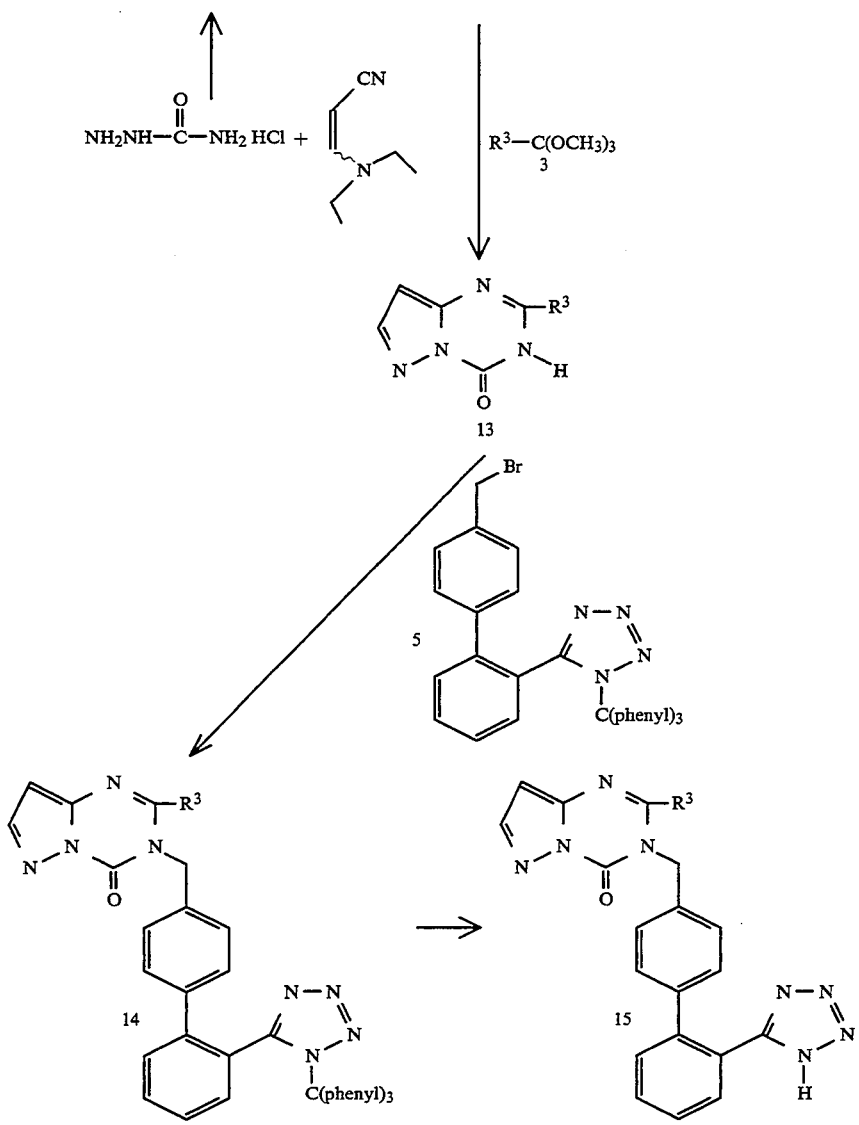

As outlined in Scheme IV, 2-substituted-7-substituted-pyrazolo[1,5-a]-1,3,5-triazin-4(1H)-one 13, is brominated in chloroform:acetic acid with bromine to give 16. Biphenyl 5 is coupled to 16 by dissolving in acetone or other suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium diisopropylamide (LDA) or lithium hexamethyldisilazide for 8–24 hours, at 20°–60° C. The obtained alkylated pyrazolo[1,5-a]-1,3,5-triazin-4(3H)-one 17 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(3H)-one 17 with a catalytic amount of hydrochloric acid or other suitable acid such as sulfuric, trifluoroacetic or hydrogen chloride for 2–24 hours to give 18. Additionally, heating 17 in tetrahydrofuran-methanol removes the trityl protecting group and affords 18.

SCHEME IV

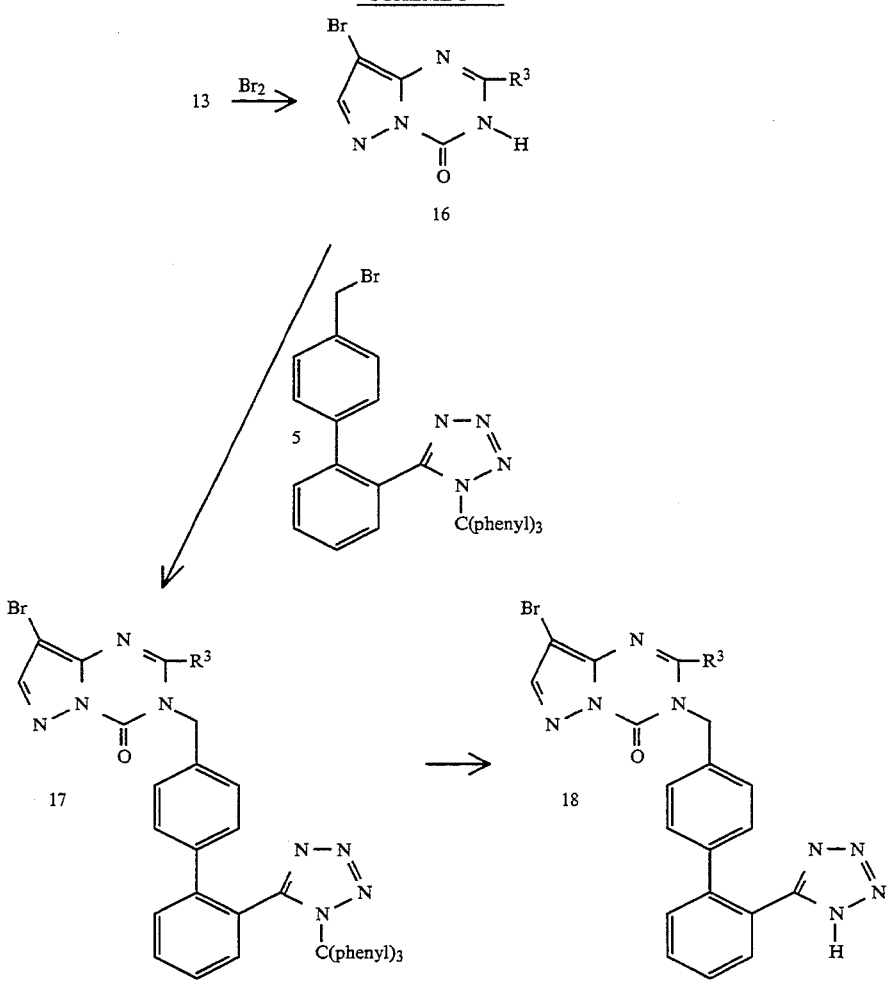

As shown in Scheme V, 13 is reacted with iodine in the presence of potassium hydroxide to give 19. Bromination of 19 with bromine in acetic acid affords 20. Reaction of 20 with tri-n-butyltin hydride gives 21.

Biphenyl 5 is coupled to 21 by dissolving in acetone or other suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium diisopropylamide (LDA) or lithium hexamethyldisilazide for 8-24 hours, at 20°-60° C. The obtained alkylated pyrazolo[1,5-a]-1,3,5-triazin-4(3H)-one 22 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(3H)-one 22 with a catalytic amount of hydrochloric acid or other suitable acid such as sulfuric, trifluoroacetic or hydrogen chloride for 2-24 hours to give 23. Additionally, heating 22 in tetrahydrofuran-methanol removes the trityl protecting group and affords 23.

Scheme V

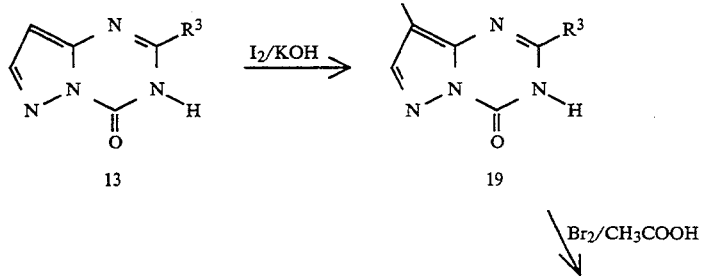

-continued
Scheme V

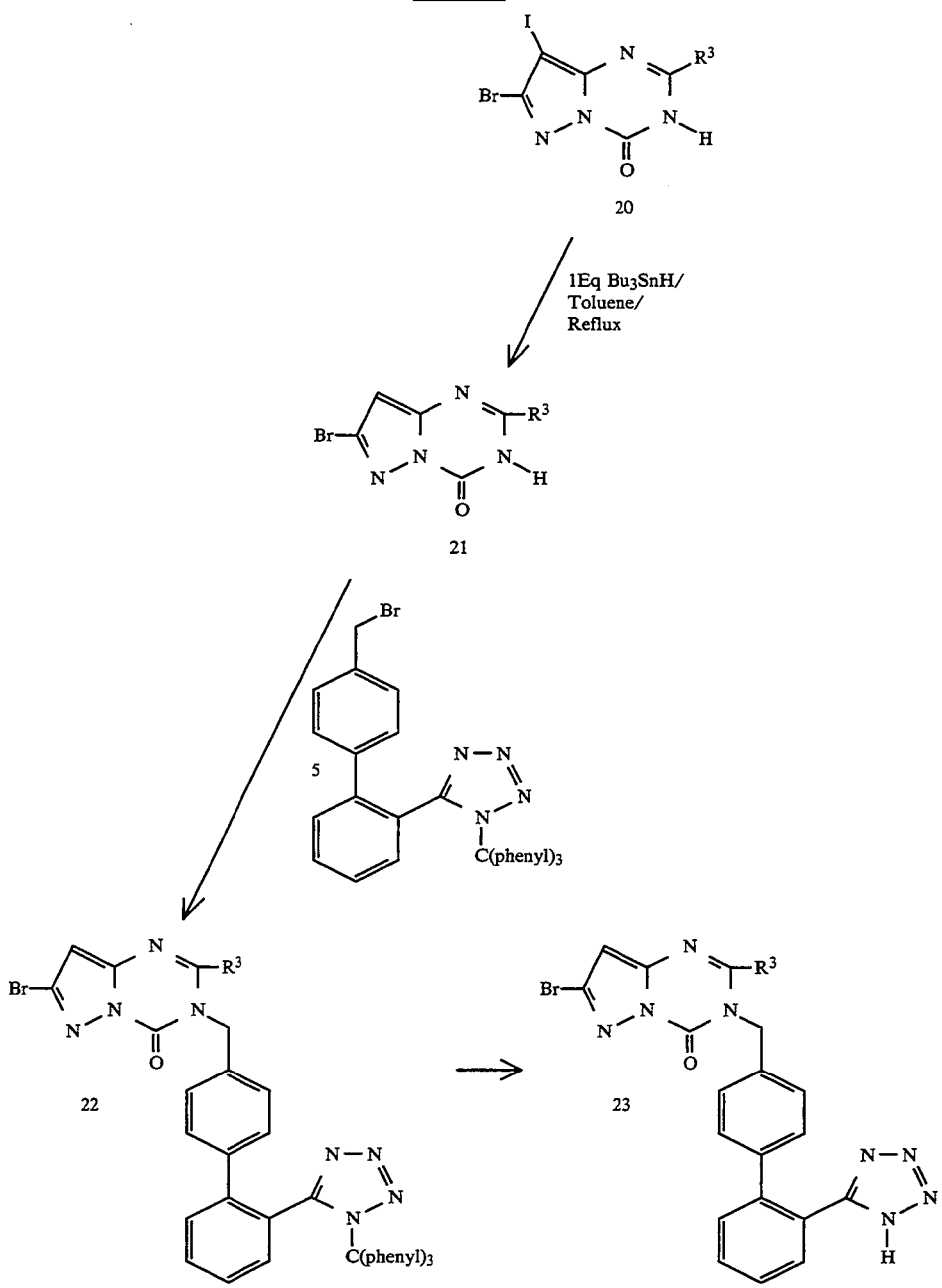

Referring to Scheme VI, 19 is reacted with tin reagent 24, where $R^2$ is lower alkyl of 1 to 4 carbon atoms, phenyl, substituted phenyl, (substitution selected from mono-lower alkyl of 1 to 3 carbon atoms, trifluoromethyl, nitro, O-alkyl of 1 to 3 carbon atoms, F, Cl, or Br), pyridine, thiophene or furan, in the presence of palladium zero to give 25.

Biphenyl 5 is coupled to 25 by dissolving in acetone or other suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium diisopropylamide (LDA) or lithium hexamethyldisilazide for 8–24 hours, at 20°–60° C. The obtained alkylated pyrazolo[1,5-a]-1,3,5-triazin-4(3H)-one 26 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(3H)-one 26 with a catalytic amount of hydrochloric acid or other suitable acid such as sulfuric, trifluoroacetic or hydrogen chloride for 2–24 hours to give 27. Additionally, heating 26 in tetrahydrofuran-methanol removes the trityl protecting group and affords 27.

Scheme VI

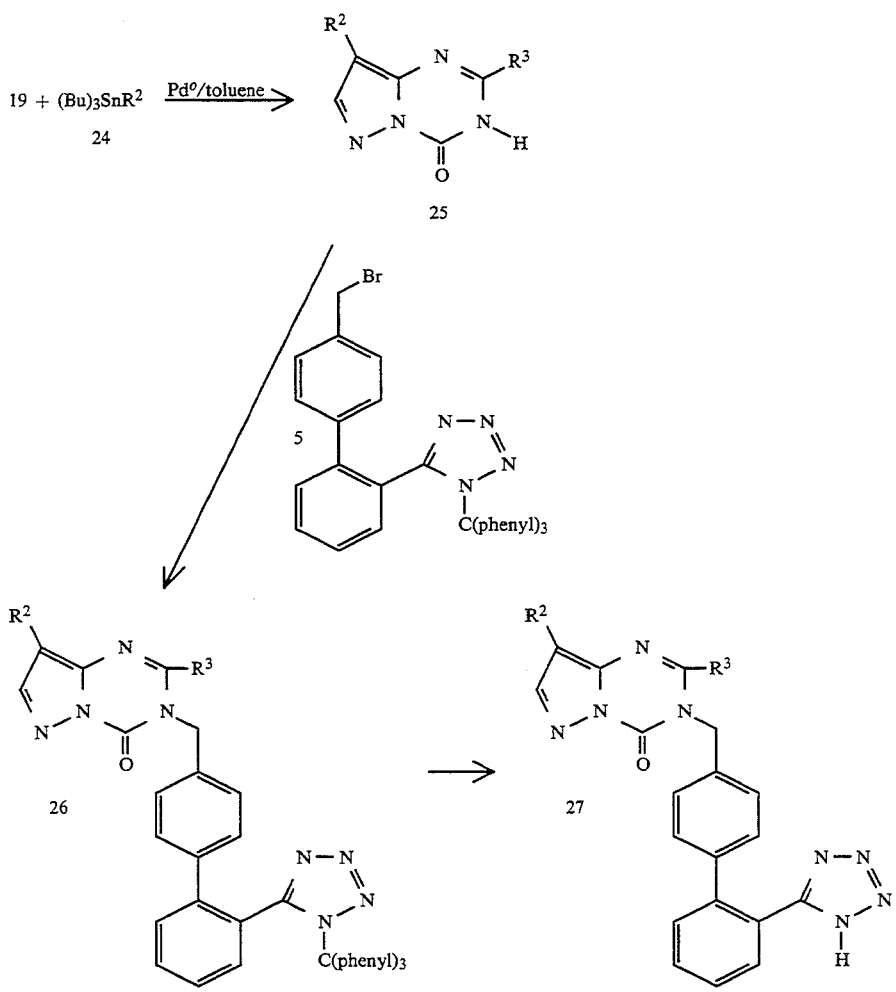

Referring to Scheme VII, 28 where R is H, lower alkyl of 1 to 3 carbon atoms, trifluoromethyl, nitro, O-alkyl of 1 to 3 carbon atoms, F, Cl or Br, is reacted with N,N-dimethylformamide dimethyl acetal to give 29. Further reaction of 29 with semicarbazide gives 30. Reaction of 30 with Z affords 31.

Biphenyl 5 is coupled to 31 by dissolving in acetone or other suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium diisopropylamide (LDA) or lithium hexamethyldisilazide for 8–24 hours, at 20°–60° C. The obtained alkylated pyrazolo[1,5-a]-1,3,5-triazin-4(3H)-one 32 may be purified by chromatography or used as is in further transformations and/or deprotection.

Deprotection of the trityl group is accomplished by refluxing an aqueous acetone solution of alkylated pyrazolo[1,5-a]-1,3,5-triazin-4(3H)-one 32 with a catalytic amount of hydrochloric acid or other suitable acid such as sulfuric, trifluoroacetic or hydrogen chloride for 2–24 hours to give 33. Additionally, heating 32 in tetrahydrofuran-methanol removes the trityl protecting group and affords 33.

Scheme VII

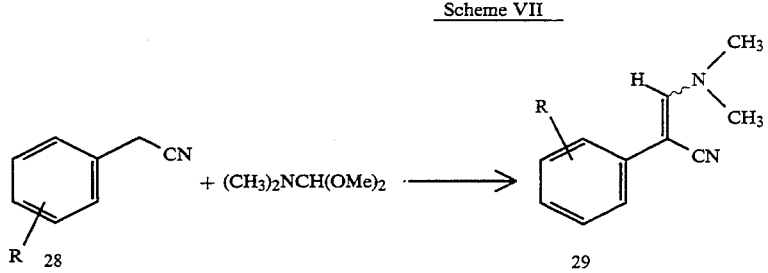

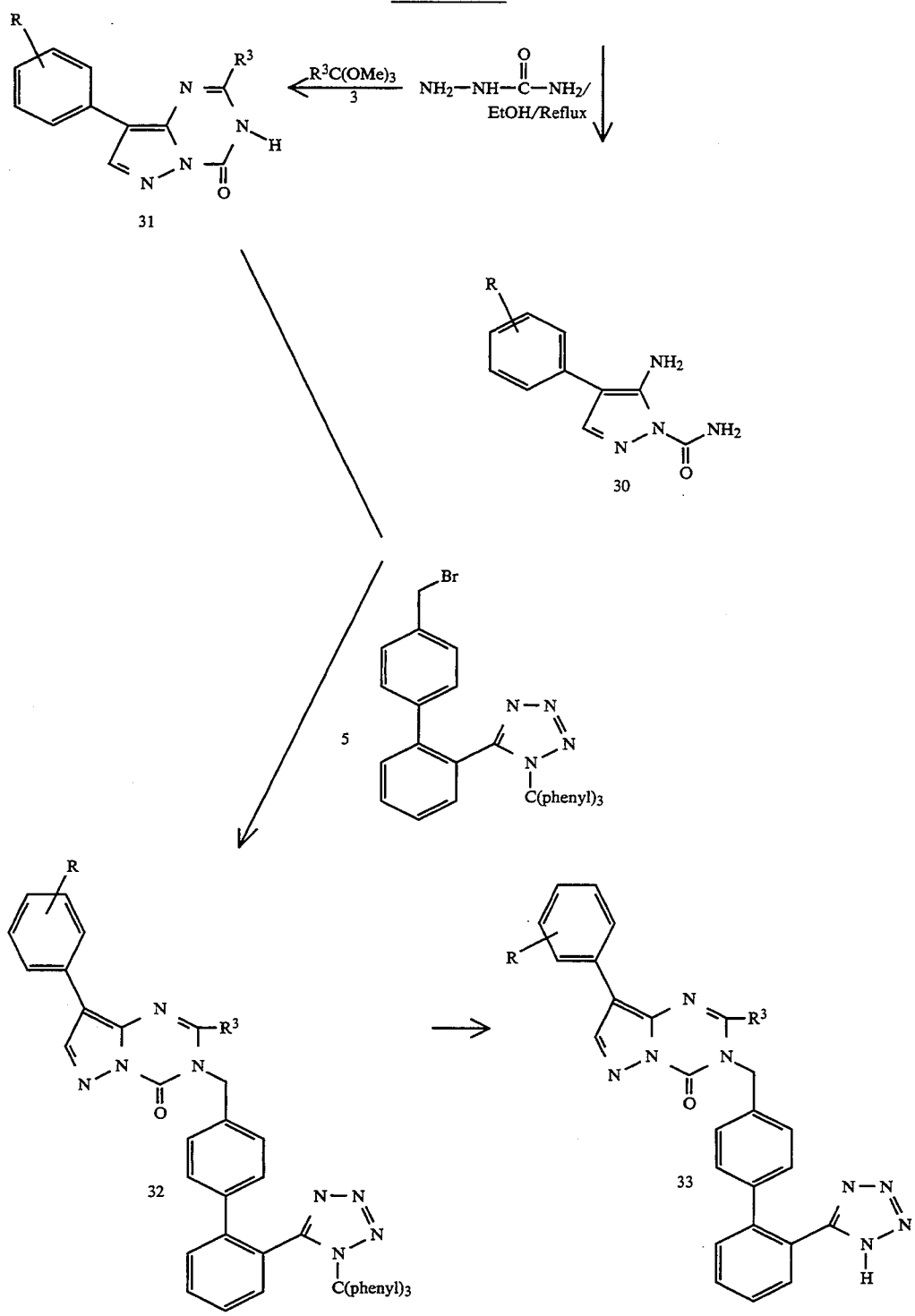
In addition, as shown in Scheme VIII 25 can be brominated to give 34, where $R^2$ and $R^3$ are hereinbefore defined, which can be alkylated with 5 under the conditions shown in Schemes I–VII to give 35 which is deblocked under the conditions shown in Schemes I–VII to give 36.

Scheme VIII
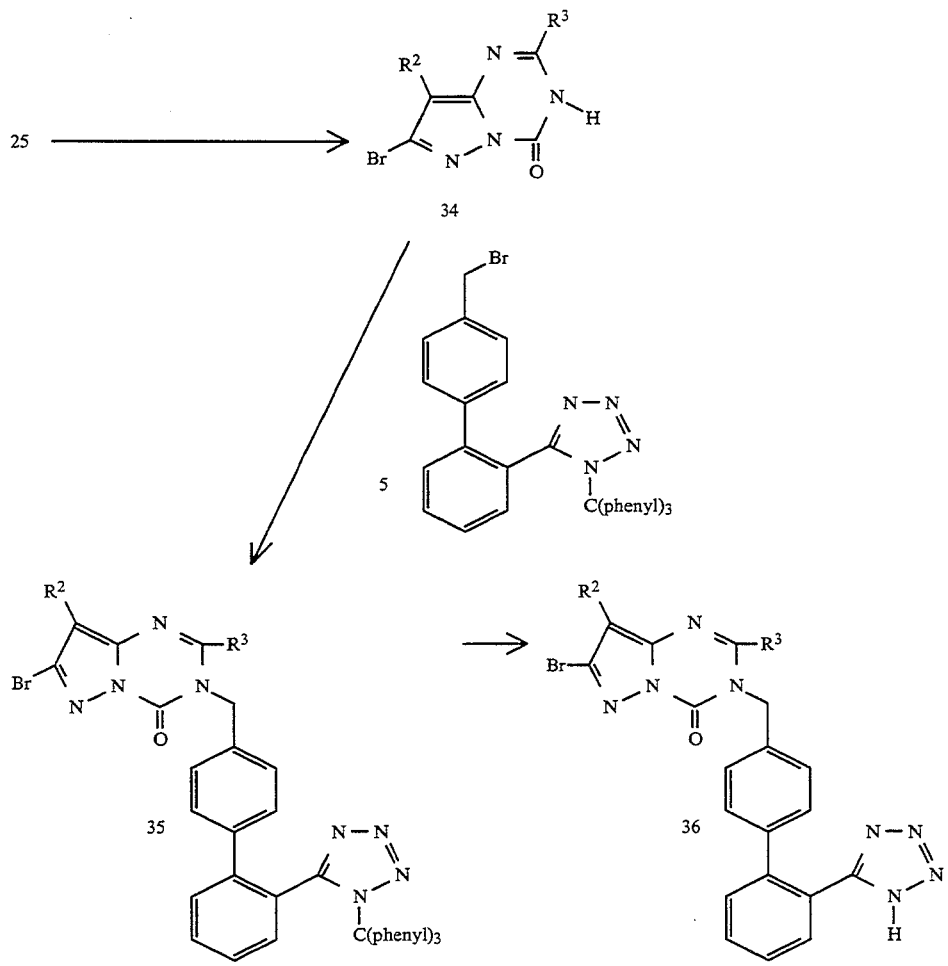
In addition as shown in Scheme IX 31 can be brominated to give 37, where R is hereinbefore defined, which can be alkylated with 5 under the conditions shown in Schemes I–VII to give 38 which is deblocked under the conditions shown in Schemes I–VII to give 39.
Scheme IX
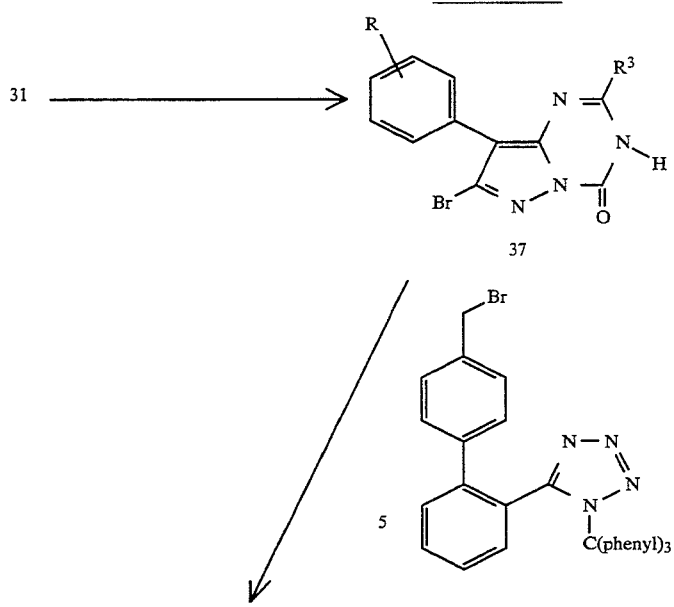

-continued
Scheme IX

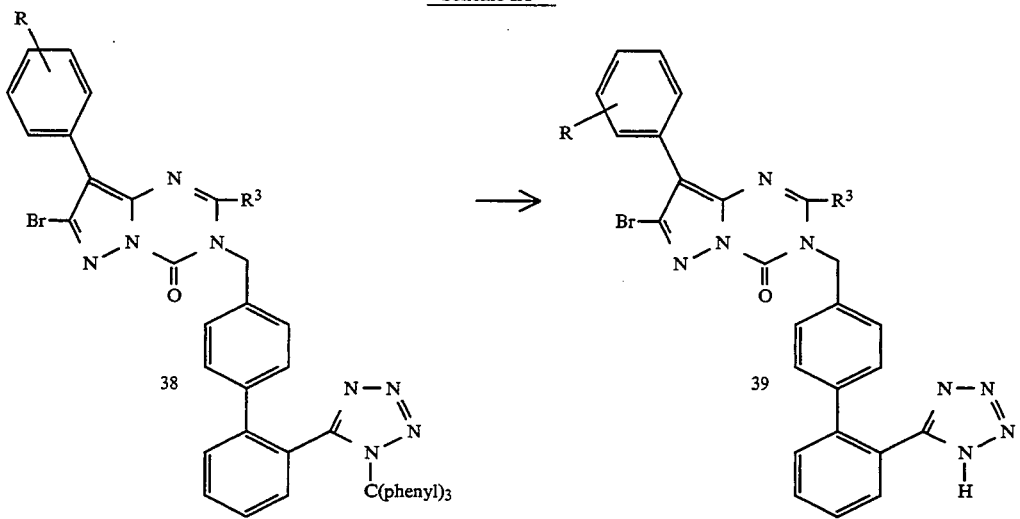

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotecting conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium, magnesium and ammonium salts.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

5-Amino-3-(2-furanyl)-1H-pyrazole-1-carboxamide

To a stirred solution of 5.5 g of semicarbazide hydrochloride in 100 ml of absolute ethyl alcohol is added 3.0 g of sodium methoxide at room temperature. The reaction mixture is stirred for 30 minutes and 6.0 g of 2-furoyl acetonitrile is added. The reaction mixture is heated at reflux for 1 hour and concentrated in vacuo to a residue. The residue is suspended in water, filtered and dried to give 6.0 g of the desired product as a solid, m.p. 145° C.

EXAMPLE 2

5-Amino-3-phenyl-1H-pyrazole-1-carboxamide

To a stirred solution of 6.0 g of semicarbazide hydrochloride in 100 ml of ethyl alcohol is added 2.8 g of sodium methoxide at room temperature. The reaction mixture is stirred for 10 minutes and 7.0 g of benzoylacetonitrile added. The reaction mixture is heated at reflux for 1 hour, cooled and concentrated in vacuo to a yellow solid. The yellow solid is suspended in water, filtered and dried. The dried solid is suspended in 100 ml of ethyl alcohol and 10 ml of triethylamine followed by heating at reflux for 1 hour. The reaction mixture is cooled and the volatiles removed in vacuo to a residue which is suspended in water, filtered, washed with water and dried to give 5.0 g of the desired product as a solid, m.p. 255° C.

EXAMPLE 3

5-Amino-3-(4-fluorophenyl)-1H-pyrazole-1-carboxamide

To a stirred solution of 12.0 g of semicarbazide hydrochloride in 200 ml of ethyl alcohol is added 5.35 g of sodium methoxide. The reaction mixture is stirred for 15 minutes and 16.3 g of p-fluorobenzoylacetonitrile added. The reaction mixture is heated at reflux for 2 hours, cooled and concentrated in vacuo to a separated solid which is filtered and washed with water and air dried. The solid is dissolved in 200 ml of ethyl alcohol and 5 ml of triethylamine followed by reflux for 1 hour. The volatiles are evaporated in vacuo to a solid which is filtered, washed with water and air dried to give 8.0 g of the desired product as a solid, m.p. 140° C.

EXAMPLE 4

2-Butyl-7-phenyl-pyrazolo[1,5-a]-1,3,5-triazin-4(1H)-one

A mixture of 4.0 g of the product of Example 2 and 10 ml of trimethylorthovalerate is heated at 130° C. for 1 hour. The reaction mixture is cooled to room temperature and diluted with 400 ml of hexanes. The resulting solid is collected, washed with hexanes and dried to give 4.0 g of the desired product as colorless crystalline solid, m.p. 234° C.

EXAMPLE 5

2-Butyl-7-(4-fluorophenyl)-pyrazolo[1,5-a][1,3,5]-triazin-4(1H)-one

A mixture of 5.0 g of the product of Example 3 and 20 ml of trimethylorthovalerate is heated at reflux for 30 minutes. The reaction mixture is cooled to room temperature and diluted with hexanes. The resulting solid is collected by filtration, washed with hexanes and dried to give 4.0 g of the desired product as a solid, m.p. 238° C.

EXAMPLE 6

2-Butyl-7-(2-furanyl)-pyrazolo[1,5-a][1,3,5]-triazin-4(1H)-one

A mixture of 3.0 g of the product of Example 1 and 10 ml of trimethylorthovalerate is heated at 130 C. for 30 minutes. The reaction mixture is cooled to room temperature and diluted with hexanes. The resulting colorless solid is collected by filtration, washed with hexanes and dried to give 2.0 g of the desired product as a solid, m.p. 190° C.

EXAMPLE 7

2-Butyl-7-phenyl-3-[[2'[1-(triphenylmethyl]-1H-tetrazol-5-yl][1,1'-bipheny]-4-yl]methyl]pyrazolo[1,5-a]-1,3,5-triazin-4(3H)-one A mixture of 536 mg of the product of Example 4 and 1.1 g of 2-butyl-6-(bromomethyl)-4-(1H)-quinazolinone in 100 ml of acetone is heated at reflux with 2.0 g of potassium carbonate for 24 hours. The reaction mixture is cooled to room temperature, filtered and the solid washed with acetone. The filtrate is concentrated in vacuo to a residue which is purified by column chromatography on silica gel by elution with 30% ethyl acetate-hexanes to give 850 mg of the desired product as a spongy solid. M+H 745

EXAMPLE 8

2-Butyl-7-(4-fluorophenyl)-3-[[2'-[1-(triphenylmethyl)-1H-tetrazol-5-yl]-[1,1'-biphenyl]-4-yl]methyl]-pyrazole-[1,5-a]-1,3,5-triazin-4(3H)-one A mixture of 500 mg of the product of Example 5 and 1.1 g of 2-butyl-6-(bromomethyl)-4-(1H)-quinazolinone in 100 ml of acetone is heated at reflux with 2.0 g of potassium carbonate for 24 hours. The reaction mixture is cooled to room temperature, filtered and the solid washed with acetone. The filtrate is concentrated in vacuo to a residue which is purified by column chromatography on silica gel by elution with 30% ethyl acetate-hexanes to give 800 mg of the desired product as a spongy solid. M+H 763

EXAMPLE 9

2-Butyl-7-(2-furanyl)-3-[[2'-[1-(triphenylmethyl)-1H-tetrazol-5-yl][1,1'-biphenyl]-4-yl]methyl-pyrazolo[1,5-a]-1,3,5-triazin-4(3H)-one A mixture of 500 mg of the product of Example 1 and 1.1 g of 2-butyl-6-(bromomethyl)-4-(1H)-quinazolinone in 100 ml of acetone is heated at reflux with 2.0 g of potassium carbonate for 24 hours. The reaction mixture is cooled to room temperature, filtered and the solid washed with acetone. The filtrate is concentrated in vacuo to a residue which is purified by column chromatography on silica gel by elution with 30% ethyl acetate-hexanes to give 750 mg of the desired product as a spongy solid. M+H 735

EXAMPLE 10

2-Butyl-7-phenyl-3-[[2'-(1H-tetrazol-5-yl)[1,1'-biphenyl]-4-yl]methyl]pyrazolo[1,5-a]-1,3,5-triazin-4(3H)-one A solution of 800 mg of the product of Example 7 in 100 ml of acetone containing 3 drops of 5% HCl is refluxed for 16 hours. The reaction mixture is concentrated in vacuo to a residue which is purified by column chromatography on silica gel by elution with 70% ethyl acetate-hexanes to give 350 mg of the desired product as a solid. M+H 503

EXAMPLE 11

2-Butyl-7-(2-furanyl)-3-[[2'-(1H-tetrazol-5-yl)[1,1'-biphenyl]-4-yl]methyl]pyrazolo[1,5-a]-1,3,5-triazin-4(3H)-one A solution of 700 mg of the product of Example 9 in 50 ml of methanol-chloroform containing 1 drop of 1% HCl is refluxed for 16 hours. The reaction mixture is concentrated in vacuo to a residue which is purified by column chromatography on silica gel by elution with 60% ethyl acetate-hexanes to give 250 mg of the desired product as a solid. M+H 493

EXAMPLE 12

2-Butyl-7-(4-fluorophenyl)-3-[[2'-(1H-tetrazol-5-yl)[1,1'-biphenyl]-4-yl]methyl]pyrazolo[1,5-a]-1,3,5-triazin-4(3H)-one A solution of 750 mg of the product of Example 8 in 100 ml of methanol-chloroform containing 2 drops of 5% HCl is refluxed for 16 hours. The reaction mixture is concentrated in vacuo to a residue which is purified by column chromatography on silica gel by elution with 60% ethyl acetate-hexanes to give 300 mg of the desired product as a solid. M+H 521.

EXAMPLE 13

2-(2-Cyanoethenyl)-hydrazinecarboxamide

To a stirred solution of 6.9 g of semicarbazide hydrochloride in 120 ml of ethyl alcohol is added 9.6 g of N,N-diethylacrylonitrile. The reaction mixture is heated at reflux for 6 hours then concentrated in vacuo to a residue which is filtered, washed with water and air dried to give 10.0 g of the desired product as a yellow solid. M+H=126.

EXAMPLE 14

5-Amino-1H-pyrazole-1-carboxamide

A solution of 5.0 g of the product of Example 13 in 50 ml of ethyl alcohol containing 3.0 ml of triethylamine is heated at reflux for 4 hours then concentrated in vacuo to a residue which is stirred with cold water. The resulting solid is filtered, washed with additional cold water and dried to give 4.0 g of the desired product as a yellow crystalline solid. M+H=127.

EXAMPLE 15

2-Butyl-pyrazolo[1,5-a]-1,3,5-triazin-4(1H)-one

A solution of 3.0 g of the product of Example 14 in 10 ml of trimethylorthovalerate is heated at 130° C. for 1 hour. The reaction mixture is cooled to room temperature and diluted with hexanes. The resulting solid is collected, washed with hexanes and dried to give 2.0 g of the desired product as a solid. M+H=193.

EXAMPLE 16

2-Butyl-3-[[2'-[1-(triphenylmethyl)-1H-tetrazol-5-yl][1,1'-biphenyl]-4-yl]methyl]-pyrazolo[1,5-a]-1,3,5-triazin-4(3H)-one A mixture of 400 mg of the product of Example 15 and 1.2 g of 2-butyl-6-(bromomethyl)-4-(1H)-quinazolinone in 100 ml of acetone is heated at reflux with 2.0 g of potassium carbonate for 8 hours. The reaction mixture is cooled to room temperature, filtered and the solid washed with acetone. The filtrate is concentrated in vacuo to a residue which is purified by column chromatography on silica gel by elution with 30% ethyl acetate-hexanes to give 800 mg of the desired product as a spongy solid. M+H=669.

EXAMPLE 17

2-Butyl-3-[[2'-(1H-tetrazol-5-yl)[1,1'-biphenyl]-4-yl]methyl]pyrazolo[1,5-a]-1,3,5-triazin-4(3H) -one A solution of 700 mg of the product of Example 16 in 200 ml of 9:1 acetone-water, 50 ml of methyl alcohol and 2 drops of 5% HCl is refluxed for 16 hours. The reaction mixture is concentrated in vacuo to a residue which is extracted with 3:1 chloroform-methanol. The chloroform layer is dried with anhydrous $Na_2SO_4$, filtered and concentrated to a residue which is purified by column chromatography on silica gel by elution with 90% ethyl acetate-hexanes to give 300 mg of the desired product as a solid. M+H=426.

EXAMPLE 18

8-Bromo-2-butyl-pyrazolo[1,5-a]-1,3,5-triazin-4(1H)-one

To a solution of 4.0 g of the product of Example 15 in 25 ml of 3:1 chloroform-acetic acid is added 1.5 ml of bromine. The reaction mixture is stirred at room temperature for 4 hours. The chloroform is removed in vacuo and the residue diluted with ice water. The resulting solid is collected, washed with water and dried to give 3.5 g of the desired product as a brown solid, m.p. 188° C.

EXAMPLE 19

8-Bromo-2-butyl-3-[[2'-[1-(triphenylmethyl)-1H-tetrazol-5-yl][1,1'-biphenyl]-4-yl]methyl]-pyrazolo[1,5-a]-1,3,5-triazin-4(3H)-one A mixture of 500 mg of the product of Example 18 and 1.1 g of 2-butyl-6-(bromoethyl)-4-(1H)-quinazolinone in 100 ml of acetone is heated at reflux with 2.0 g of potassium carbonate for 24 hours. The reaction mixture is cooled to room temperature, filtered and the solid washed with acetone. The filtrate is concentrated in vacuo to a residue which is purified by column chromatography on silica gel by elution with 30% ethyl acetate-hexanes to give 850 mg of the desired product as a spongy solid. M+H 750.

EXAMPLE 20

8-Bromo-2-butyl-3-[[2'-(1H-tetrazol-5-yl)-[1,1,-biphenyl]-4-yl]methyl-pyrazolo-[1,5-a]-1,3,5-triazin-4(3H)-one A solution of 800 mg of the product of Example 19 in 100 ml of 1:1 acetone-methanol containing 2 drops of 5% HCl is refluxed for 16 hours. The reaction mixture is concentrated in vacuo to a residue which is purified by column chromatography on silica gel by elution with 50% ethyl acetate-hexanes to give 350 mg of the desired product as a solid, m.p. 121° C.

EXAMPLE 21

2-Butyl-3-[[2'-(1H-tetrazol-5-yl)-[[1,1'-biphenyl]-4-yl]methyl]-pyrazolo[1,5-a]-1,3,5-triazin-4(3H)-one potassium salt To a stirred solution of 426 mg of 2-butyl-3-[[2'-(1H-tetrazol-5-yl)-[[1,1'-biphenyl]-4yl]-4-yl]methyl]-pyrazolo[1,5-a]-1,3,5-triazin-4(3H)-one in 50 ml of ethyl alcohol is added 56 mg of potassium hydroxide. The reaction mixture is heated at reflux for 15 minutes and evaporated .in vacuo to a residue which is dried to give 460 mg of the desired product as a solid M+H 465.

Angiotensin II Antagonists In Vitro Tests

Materials and Methods

Beef adrenals are obtained from a local slaughter house (Maxwell-Cohen). [$^{125}$I](Sar$^1$,Ile$^8$)AngII, S.A. 2200 Ci/mmole, is purchased from Dupont (NEN®, Boston, Mass.). all unlabeled AngII analogs, Dimethylsulfoxide (DMSO), nucleotides, bovine serum albumin (BSA) are purchased from Sigma Chemical Co , St Louis, Mo. U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor driven teflon pestle with a clearance of 1.0 mm. The homogenate is centrifuged first at low speed (3,000×g) for 10 minutes. The resulting pellet is discarded and the supernatant fluid recentrifuged at 10,000×g of 15 minutes to give a $P_2$ pellet. This $P_2$ pellet is discarded and the liquid phase is carefully decanted off in clean centrifuge tubes and recentrifuged at high speed (100,000×g) for 60 minutes. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Farr, A. L. and Randall, R. J., Protein measurement with Folin phenol reagent. J. Biol. Chem., 48, 265–275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of[$^{125}$I](Sar$^1$,Ile$^8$)AngII

The binding of [$^{125}$I](Sar$^1$ Ile$^8$)AngII to microsomal membranes is initiated by the addition of reconstituted membranes (1:10 vols.) in freshly made 50.0 mMTris.HCl buffer, pH 7.4 containing 0.25% heat inactivated bovine serum albumin (BSA): 80 ul membrane protein (10 to 20 ug/assay) to wells already containing 100 ul of incubatin buffer (as described above) and 20 ul [$^{125}$I](Sar$^1$,Ile$^8$)AngII (Specific Activity 2200 Ci/m-mole). Non-specific binding is measured in the presence of 1.0 uM unlabeled (Sar$^1$,Ile$^8$)AngII, added in 20 ul volume. Specific binding for [$^{125}$I](Sar$^1$, Ile$^8$)AngII is greater than 90% In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$, Ile$^8$)AngII to the membranes. Assays are performed in triplicate. The wells are left undisturbed for 60 minutes at room temperature. Following incubation, all wells are harvested at once with a Brandel ® Harvester especially designed for a 96 well plate (Brandel ®Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduced the radioactivity retained by the filter blanks. This method is routinely used. The filters are removed from the filter grid and counted in a Parkard ® Cobra Gamma Counter for 1 minute. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 µM are considered active compounds and are then evaluated in concentration-response experiments to determine their IC$_{50}$ values. The results are shown in Table I.

TABLE I

| Example No. | Angiotensin II Receptor Binding IC$_{50}$(M) |
| --- | --- |
| 10 | 7.6 × 10$^{-7}$ |
| 11 | 6.7 × 10$^{-7}$ |
| 12 | 6.3 × 10$^{-8}$ |
| 17 | 1.2 × 10$^{-6}$ |
| 20 | 4.0 × 10$^{-6}$ |
| 21* | 3.0 × 10$^{-6}$ |

*Potassium salt

As can be seen from the above table, the compounds demonstrate excellent activity.

The enzyme renin acts on a blood plasma a$_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

As can be seen from Table I, the compounds demonstrate excellent Angiotensin II Receptor Binding activity.

The enzyme renin acts on a blood plasma a$_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male Okamoto-Aoki SHR, 16-20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10-20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to s Statham P23Db pressure transducer, and pulsatile blood pressure is recorded to 10-15 minutes with a Gould Brush recorder. (Chan et al., (Drug Development Res., 18:75-94, 1989).

Angiotensin II (human sequence, Sigma Chem. Co., St. Louis, Mo.) of 0.05 and 0.1 ug/kg i.v. is injected into all rats (predosing response.). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

TABLE II

| | ANGIOTENSIN II (AII) VASOPRESSOR RESPONSE | | | | | | | |
| --- | --- | --- | --- | --- | --- | --- | --- | --- |
| | Dose (mg/kg) | AII Dose mcg/kg | Min Post Dose | Control Before AII | Response After AII | Change | Average Change | % Inhibition |
| CONTROL | | 0.05 | 0 | 220 | 270 | 50 | 50 | 80 |
| | | | | 205 | 255 | 50 | | |
| | | 0.1 | | 215 | 275 | 60 | 50 | |
| | | | | 210 | 250 | 40 | | |
| Ex. 10 | 10 i.v. | 0.05 | 30 | 220 | 235 | 15 | 10 | 80 |
| | | | | 210 | 215 | 5 | | |
| | | 0.1 | | 210 | 245 | 35 | 20 | 60 |
| | | | | 210 | 215 | 5 | | |
| | | 0.05 | 60 | 210 | 255 | 45 | 30 | 40 |
| | | | | 215 | 230 | 15 | | |
| | | 0.1 | | 210 | 250 | 40 | 25 | 50 |

TABLE II-continued

ANGIOTENSIN II (AII) VASOPRESSOR RESPONSE

| | Dose (mg/kg) | AII Dose mcg/kg | Min Post Dose | Control Before AII | Response After AII | Change | Average Change | % Inhibition |
|---|---|---|---|---|---|---|---|---|
| | | | | 205 | 215 | 10 | | |
| Ex. 10 | 20 i.v. | 0.05 | 90 | 195 | 205 | 10 | 10 | 80 |
| | | | | 205 | 215 | 10 | | |
| | | 0.1 | | 205 | 215 | 10 | 5 | 90 |
| | | | | 210 | 210 | 0 | | |
| | | 0.05 | 120 | 175 | 185 | 10 | 15 | 70 |
| | | | | 190 | 210 | 20 | | |
| | | 0.1 | | 200 | 205 | 5 | 7.5 | 85 |
| | | | | 190 | 200 | 10 | | |
| | | 0.05 | 180 | 185 | 195 | 10 | 17.5 | 65 |
| | | | | 185 | 210 | 25 | | |
| | | 0.1 | | 190 | 210 | 20 | 17.5 | 65 |
| | | | | 185 | 200 | 15 | | |
| | | 0.05 | 240 | 195 | 205 | 10 | 7.5 | 85 |
| | | | | 185 | 190 | 5 | | |
| CONTROL | | 0.1 | | 200 | 217 | 17 | 13.5 | 73 |
| | | | | 185 | 195 | 10 | | |
| | | 0.05 | 300 | 190 | 220 | 30 | 22.5 | 55 |
| | | | | 180 | 195 | 15 | | |
| | | 0.1 | | 205 | 235 | 30 | 30 | 40 |
| | | | | 175 | 205 | 30 | | |

SPONTANEOUSLY HYPERTENSIVE RATS n = 2 Body weight(s): 350,350 grams

| | Dose (mg/kg) | AII Dose mcg/kg | Min Post Dose | Control Before AII | Response After AII | Change | Average Change | % Inhibition |
|---|---|---|---|---|---|---|---|---|
| CONTROL | | 0.05 | 0 | 200 | 245 | 45 | 37.5 | |
| | | | | 190 | 220 | 30 | | |
| | | 0.1 | | 200 | 255 | 55 | 47.5 | |
| | | | | 195 | 235 | 40 | | |
| Ex. 11 | 10 i.v. | 0.05 | 30 | 200 | 200 | 0 | 0 | 100 |
| | | | | 205 | 205 | | | |
| | | 0.1 | | 190 | 192 | 2 | 1 | 98 |
| | | | | 205 | 205 | 0 | | |
| | | 0.05 | 60 | 185 | 198 | 13 | 9 | 76 |
| | | | | 195 | 200 | 5 | | |
| | | 0.1 | | 195 | 205 | 10 | 10 | 79 |
| | | | | 195 | 205 | 10 | | |
| | | 0.05 | 90 | 190 | 200 | 10 | 12.5 | 67 |
| | | | | 185 | 200 | 15 | | |
| | | 0.1 | | 190 | 210 | 20 | 17.5 | 63 |
| | | | | 190 | 205 | 15 | | |
| | | 0.05 | 120 | 185 | 205 | 20 | 15 | 60 |
| | | | | 185 | 195 | 10 | | |
| | | 0.1 | | 185 | 205 | 20 | 17.5 | 63 |
| | | | | 185 | 200 | 15 | | |
| | | 0.05 | 180 | 185 | 195 | 10 | 15 | 60 |
| | | | | 185 | 205 | 20 | | |
| | | 0.1 | | 185 | 210 | 25 | 25 | 47 |
| | | | | 185 | 210 | 25 | | |
| | | 0.05 | 240 | 185 | 210 | 25 | 20 | 47 |
| CONTROL | | | | 185 | 200 | 15 | | |
| | | 0.1 | | 175 | 205 | 30 | 27.5 | 42 |
| | | | | 185 | 210 | 25 | | |
| | | 0.05 | 300 | 185 | 215 | 30 | 25 | 33 |
| | | | | 185 | 205 | 20 | | |
| | | 0.1 | | 185 | 210 | 25 | 27.5 | 42 |
| | | | | 185 | 215 | 30 | | |

SPONTANEOUSLY HYPERTENSIVE RATS n = 2 Body weight(s): 260,290 grams

| | Dose (mg/kg) | AII Dose mcg/kg | Min Post Dose | Control Before AII | Response After AII | Change | Average Change | % Inhibition |
|---|---|---|---|---|---|---|---|---|
| CONTROL | | 0.05 | 0 | 185 | 235 | 50 | 55 | |
| | | | | 225 | 285 | 60 | | |
| | | 0.1 | | 175 | 230 | 55 | 52.5 | |
| | | | | 235 | 285 | 50 | | |
| Ex. 12 | 10 i.v. | 0.05 | 30 | 195 | 205 | 10 | 15 | 73 |
| | | | | 225 | 245 | 20 | | |
| | | 0.1 | | 200 | 210 | 10 | 12.5 | 76 |
| | | | | 235 | 250 | 15 | | |
| | | 0.05 | 60 | 180 | 200 | 20 | 15 | 7 |
| | | | | 230 | 240 | 10 | | |
| | | 0.1 | | 190 | 205 | 15 | 22.5 | 57 |
| | | | | 220 | 250 | 30 | | |
| | | 0.05 | 90 | 165 | 185 | 20 | 22.5 | 59 |
| | | | | 225 | 250 | 25 | | |
| | | 0.1 | | 170 | 200 | 30 | 27.5 | 48 |
| | | | | 235 | 260 | 25 | | |
| | | 0.0 | 120 | 160 | 185 | 25 | 27.5 | 50 |
| | | | | 225 | 255 | 30 | | |
| | | 0.1 | | 170 | 195 | 25 | 33.5 | 36 |
| | | | | 225 | 267 | 42 | | |
| | | 0.05 | 180 | 185 | 195 | 10 | 21.5 | 61 |
| | | | | 207 | 240 | 33 | | |
| | | 0.1 | | 185 | 200 | 15 | 27.5 | 48 |
| | | | | 210 | 250 | 40 | | |

TABLE II-continued

ANGIOTENSIN II (AII) VASOPRESSOR RESPONSE

| | Dose (mg/kg) | AII Dose mcg/kg | Min Post Dose | Control Before AII | Response After AII | Change | Average Change | % Inhibition |
|---|---|---|---|---|---|---|---|---|
| | | 0.05 | 240 | 185 | 195 | 10 | 22.5 | 59 |
| CONTROL | | | | 220 | 255 | 35 | | |
| | | 0.1 | | 185 | 200 | 15 | 30 | 43 |
| | | | | 225 | 270 | 45 | | |
| | | 0.05 | 300 | 185 | 200 | 15 | 25 | 55 |
| | | | | 225 | 260 | 35 | | |
| | | 0.1 | | 185 | 205 | 20 | 35 | 33 |
| | | | | 225 | 275 | 50 | | |
| SPONTANEOUSLY HYPERTENSIVE RATS n = 2 Body weight(s): 380,380 grams | | | | | | | | |
| CONTROL | | 0.05 | 0 | 250 | 295 | 45 | 47.5 | |
| | | | | 245 | 295 | 50 | | |
| | | 0.1 | | 250 | 290 | 40 | 47.5 | |
| | | | | 220 | 275 | 55 | | |
| Ex. 17 | 3 i.v. | 0.05 | 30 | 252 | 285 | 33 | 31.5 | 34 |
| | | | | 235 | 265 | 30 | | |
| | | 0.1 | | 255 | 280 | 25 | 30 | 37 |
| | | | | 225 | 260 | 35 | | |
| Ex. 17 | 10 i.v. | 0.05 | 60 | 250 | 255 | 5 | 7.5 | 84 |
| | | | | 235 | 245 | 10 | | |
| | | 0.1 | | 255 | 260 | 5 | 7.5 | 84 |
| | | | | 225 | 235 | 10 | | |
| | | 0.05 | 90 | 250 | 275 | 25 | 25 | 47 |
| | | | | 230 | 255 | 25 | | |
| | | 0.1 | | 250 | 265 | 15 | 25 | 47 |
| | | | | 225 | 260 | 35 | | |
| | | 0.05 | 120 | 245 | 270 | 25 | 27.5 | 42 |
| | | | | 225 | 255 | 30 | | |
| | | 0.1 | | 250 | 275 | 25 | 27.5 | 42 |
| | | | | 230 | 260 | 30 | | |
| | | 0.05 | 180 | 240 | 260 | 20 | 25 | 47 |
| | | | | 210 | 240 | 30 | | |
| | | 0.1 | | 240 | 270 | 30 | 35 | 26 |
| | | | | 225 | 265 | 40 | | |
| CONTROL | | 0.05 | 240 | 245 | 270 | 25 | 20 | 58 |
| | | | | 235 | 250 | 15 | | |
| | | 0.1 | | 255 | 290 | 35 | 32.5 | 32 |
| | | | | 240 | 270 | 30 | | |
| | | 0.05 | 300 | 250 | 290 | 40 | 35 | 26 |
| | | | | 215 | 245 | 30 | | |
| | | 0.1 | | 250 | 285 | 35 | 30 | 37 |
| | | | | 235 | 260 | 25 | | |
| SPONTANEOUSLY HYPERTENSIVE RATS n = 2 Body weight(s): 415,410 grams | | | | | | | | |
| CONTROL | | 0.05 | 0 | 225 | 270 | 45 | 40 | |
| | | | | 210 | 245 | 35 | | |
| | | 0.1 | | 210 | 270 | 60 | 62.5 | |
| | | | | 180 | 245 | 65 | | |
| Ex. 20 | 10 i.v. | 0.05 | 30 | 207 | 245 | 38 | 26.5 | 34 |
| | | | | 200 | 215 | 15 | | |
| | | 0.1 | | 215 | 260 | 45 | 40 | 36 |
| | | | | 200 | 235 | 35 | | |
| Ex. 20 | 20 i.v. | 0.05 | 60 | 195 | 215 | 20 | 20 | 50 |
| | | | | 180 | 200 | 20 | | |
| | | 0.1 | | 200 | 215 | 15 | 17.5 | 72 |
| | | | | 180 | 200 | 20 | | |
| | | 0.05 | 90 | 215 | 225 | 10 | 17.5 | 56 |
| | | | | 175 | 200 | 25 | | |
| | | 0.1 | | 205 | 245 | 40 | 35 | 44 |
| | | | | 185 | 215 | 30 | | |
| | | 0.05 | 120 | 205 | 250 | 45 | 32.5 | 19 |
| | | | | 195 | 215 | 20 | | |
| | | 0.1 | | 215 | 250 | 35 | 27.5 | 56 |
| | | | | 195 | 215 | 20 | | |
| | | 0.05 | 180 | 185 | 225 | 40 | 32.5 | 19 |
| | | | | 185 | 210 | 25 | | |
| | | 0.1 | | 195 | 225 | 30 | 45 | 28 |
| | | | | 165 | 225 | 60 | | |
| CONTROL | | 0.05 | 240 | 185 | 230 | 45 | 42.5 | −6 |
| | | | | 185 | 225 | 40 | | |
| | | 0.1 | | 200 | 260 | 60 | 57.5 | 8 |
| | | | | 190 | 245 | 55 | | |
| | | 0.05 | 300 | 190 | 240 | 50 | 42.5 | −6 |
| | | | | 200 | 235 | 35 | | |
| | | 0.1 | | 220 | 265 | 45 | 50 | 20 |
| | | | | 190 | 245 | 55 | | |
| SPONTANEOUSLY HYPERTENSIVE RATS n = 2 Bodyweight(s): 360,360 grams | | | | | | | | |
| CONTROL | | 0.05 | 0 | 255 | 290 | 35 | 42.5 | |
| | | | | 240 | 290 | 50 | | |
| | | 0.1 | | 225 | 277 | 52 | 53.5 | |
| | | | | 230 | 285 | 55 | | |

TABLE II-continued

ANGIOTENSIN II (AII) VASOPRESSOR RESPONSE

| | Dose (mg/kg) | AII Dose mcg/kg | Min Post Dose | Control Before AII | Response After AII | Change | Average Change | % Inhibition |
|---|---|---|---|---|---|---|---|---|
| Ex. 21 | 10 i.v. | 0.05 | 30 | 215 | 220 | 5 | 15 | 65 |
| | | | | 200 | 225 | 25 | | |
| | | 0.1 | | 210 | 225 | 15 | 22.5 | 58 |
| | | | | 200 | 230 | 30 | | |
| | | 0.05 | 60 | 210 | 235 | 25 | 32.5 | 24 |
| | | | | 210 | 250 | 40 | | |
| | | 0.1 | | 225 | 245 | 20 | 25 | 53 |
| | | | | 225 | 255 | 30 | | |
| | | 0.05 | 90 | 210 | 230 | 20 | 20 | 53 |
| | | | | 240 | 260 | 20 | | |
| | | 0.1 | | 215 | 245 | 30 | 32.5 | 39 |
| | | | | 225 | 260 | 35 | | |
| | | 0.05 | 120 | 220 | 240 | 20 | 25 | 41 |
| | | | | 225 | 255 | 30 | | |
| | | 0.1 | | 220 | 255 | 35 | 37.5 | 30 |
| | | | | 225 | 265 | 40 | | |
| | | 0.05 | 180 | 224 | 245 | 21 | 33 | 22 |
| | | | | 210 | 255 | 45 | | |
| | | 0.1 | | 225 | 255 | 30 | 32.5 | 39 |
| | | | | 240 | 275 | 35 | | |
| | | 0.05 | 240 | 220 | 245 | 25 | 30 | 29 |
| CONTROL | | | | 215 | 250 | 35 | | |
| | | 0.1 | | 225 | 265 | 40 | 40 | 25 |
| | | | | 220 | 260 | 40 | | |
| | | 0.05 | 300 | 214 | 245 | 31 | 35.5 | 16 |
| | | | | 210 | 250 | 40 | | |
| | | 0.1 | | 215 | 265 | 50 | 55 | −3 |
| | | | | 220 | 280 | 60 | | |

SPONTANEOUSLY HYPERTENSIVE RATS n = 2 Body weight(s): 450,410 grams

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar and elixirs containing, for example, from about 20 to 50% ethanol, and the like, or parenterally in the form of sterile injectable solutions or suspension containing from about 0.05 to 5% suspending agent in a isotonic medium. Such pharmaceutical preparations may contain, for example, from about 0.05 up to about 90% of the active ingredient in combination with carriers, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times day, or in sustained release form. For most large mammals the total daily dosage is from about 1 to 100 mg, preferably from 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and koalin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agent's coloring agents, preserving agents, and antioxidans, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersion can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersions medium containing, for example, water, ethanol, polyol (e.g., glycerol, propylene glycol and liquid polyethylene glycol), suitable mixtures, thereof, and vegetable oils.

What is claimed is:

1. A pyrazolo[1,5-a]-1,3,5-triazin-4(3H)-one compound having the formula:

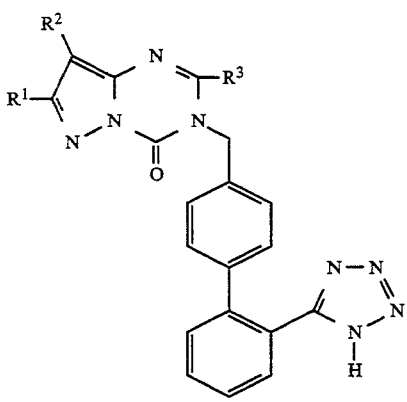

wherein:
R¹ is selected from H, lower alkyl of 1 to 4 carbon atoms, phenyl, substituted phenyl, (substitution selected from mono lower alkyl of 1 to 3 carbon atoms, trifluoromethyl, nitro, O-alkyl of 1 to 3 carbon atoms, F, Cl, and Br), pyridinyl, thienyl, furanyl, Br or Cl;

R² is selected from H, lower alkyl of 1 to 4 carbon atoms, phenyl, substituted phenyl, (substitution selected from mono-lower alkyl of 1 to 3 carbon atoms, trifluoromethyl, nitro, O-alkyl of 1 to 3 carbon atoms, F, Cl or Br), pyridinyl, thienyl, furanyl, Br and Cl;

R³ is lower alkyl of 3 to 5 carbon atoms; or the pharmaceutically acceptable salts thereof.

2. The compound according to claim 1 wherein said salts are selected from potassium, sodium, calcium, magnesium or ammonium.

3. The compound according to claim 1 wherein R³ is a straight chain alkyl of 3 or 4 carbon atoms; R¹ is selected from H, phenyl, 2-furanyl, or 4-fluorophenyl; and R² is H, or Br.

4. The compound according to claim 1, 2-butyl-7-phenyl-3-[[2'-(1H-tetrazol-5-yl)[1,1'-biphenyl]-4-yl]methyl]pyrazolo[1,5-a]-1,3,5-triazin-4(3H)-one.

5. The compound according to claim 1, 2-butyl-7-(2-furanyl) -3-[[2'-(1H-tetrazol-5-yl)[1,1'-biphenyl]-4-yl]methyl]pyrazolo-[1,5-a]-1,3,5-triazin-(4(3H) -one.

6. The compound according to claim 1, 2-butyl-7-(4-fluorophenyl)-3-[[2'-(1H-tetrazol-5-yl)[1,1'-biphenyl]-4-yl]methyl]pyrazolo-[1,5-a]-1,3,5-triazin-4(3H)-one.

7. The compound according to claim 1, 2-butyl-3-[[2'-(1H-tetrazol-5-yl)[1,1'-biphenyl]-4-yl]methyl]-pyrazolo[1,5-a]-1,3,5-triazin-4(3H)-one.

8. The compound according to claim 1, 8-bromo-2-butyl-3-[[2'-(1H-tetrazol-5-yl)-[1,1'-biphenyl]-4-yl]methyl-pyrazolo-[1,5-a]-1,3,5-triazin-4(3H)-one.

9. The compound according to claim 1, 2-butyl-3-[[2'-(1H-tetrazol-5-yl)-[[1,1'-biphenyl]-4-yl]methyl]-pyrazolo[1,5-a]-1,3,5-triazin-4(3H)-one potassium salt.

10. A pyrazolo[1,5-a]-1,3,5-triazin-4(3H)-one compound having the formula:

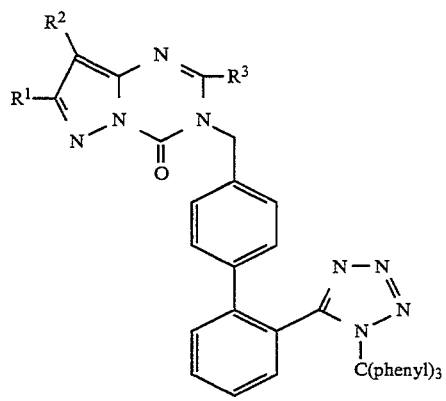

wherein:
R¹ is selected from H, lower alkyl of 1 to 4 carbon atoms, phenyl, substituted phenyl, (substitution selected from mono lower alkyl of 1 to 3 carbon atoms, trifluoromethyl, nitro, O-alkyl of 1 to 3 carbon atoms, F, Cl, and Br), pyridinyl, thienyl, furanyl, Br or Cl;

R² is H, lower alkyl of 1 to 4 carbon atoms, phenyl, substituted phenyl, (substitution selected from monolower alkyl of 1 to 3 carbon atoms, trifluoromethyl, nitro, O-alkyl of 1 to 3 carbon atoms, F, Cl and Br), pyridinyl, thienyl, furanyl, Br and Cl; R³ is lower alkyl of 3 to 5 carbon atoms.

11. The compound according to claim 10, 2-butyl-7-phenyl-3-[[2'-[1-(triphenylmethyl)-1H-tetrazol-5-yl][1,1'-biphenyl]-4-yl]methyl]-pyrazolo-[1,5-a]-1,3,5-triazin-4(3H)-one.

12. The compound according to claim 10, 2-butyl-7-(4-fluorophenyl)-3-[[2'-[1-(triphenylmethyl)-1H-tetrazol-5-yl]-[1,1'-biphenyl]-4-yl]methyl]-pyrazole-[1,5-a]-1,3,5-triazin-4(3H)-one.

13. The compound according to claim 10, 2-butyl-7-(2-furanyl)-3-[[2'-[1-(triphenylmethyl)-1H-tetrazol-5-yl][1,1'-biphenyl]-4-yl]methylpyrazolo[1,5-a]-1,3,5-triazin-4(3H)-one.

14. The compound according to claim 10, 2-butyl-3-[[2'-[1-(triphenylmethyl)-1H-tetrazol-5-yl][1,1'-biphenyl]-4-yl]methyl]-pyrazolo[1,5-a]-1,3,5-triazin-4(3H)-one.

15. The compound according to claim 10, 8-bromo-2-butyl-3-[[2'-[1-(triphenylmethyl)-1H-tetrazol-5-yl][1,1'-biphenyl]-4-yl]methyl]-pyrazolo-[1,5-a]-1,3,5-triazin-4(3H)-one.

16. A pharmaceutical composition useful for treating angiotensin induced hypertension or congestive heart failure in a mammal comprising a suitable pharmaceutical carrier and an effective amount of a compound of claim 1.

17. A method of treating angiotensin induced hypertension in a mammal comprising administering a compound of claim 1 to said mammal an amount effective to lower angiotensin induced hypertension.

18. A method of treating congestive heart failure in a mammal comprising administering a compound of claim 1 to said mammal in an amount effective to treat congestive heart failure.

19. A method of antagonizing the effects of Angiotensin II in a mammal comprising administering a compound of claim 1 to said mammal in an amount effective to antagonist the effects of Angiotensin II.

20. A process for preparing a compound of claim 1, which comprises reacting a compound of the formula:

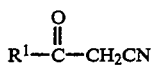

wherein $R^1$ is defined in claim 1, with semicarbazide to obtain an intermediate of the formula:

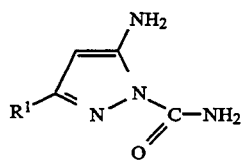

which is reacted with a compound of the formula:

$R^3-C(OCH_3)_3$ wherein $R^3$ is defined in claim 1, to obtain an intermediate of the formula:

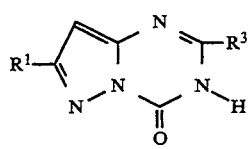

which is reacted with a compound of the formula:

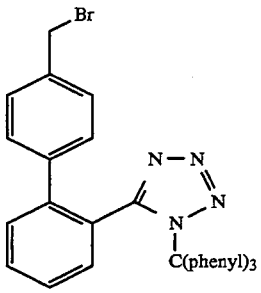

to obtain an intermediate of the formula:

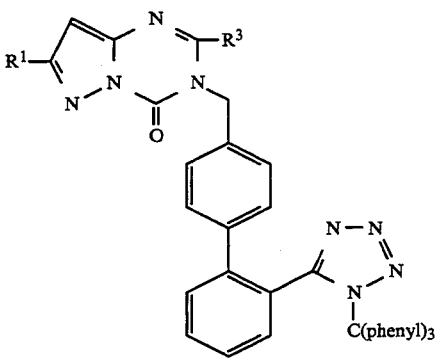

which is deblocked to give a compound of claim 1.

* * * * *